US011883650B1

(12) United States Patent
Wang et al.

(10) Patent No.: US 11,883,650 B1
(45) Date of Patent: Jan. 30, 2024

(54) BI-LAYERED NEURAL INTERFACE WITH NERVE-FACING DRUG ELUTING STRUCTURE

(71) Applicant: Verily Life Sciences LLC, South San Francisco, CA (US)

(72) Inventors: Xianyan Wang, San Jose, CA (US); Cindy Au, Redwood City, CA (US)

(73) Assignee: Verily Life Sciences, LLC, South San Francisco, CA (US)

( * ) Notice: Subject to any disclaimer, the term of this patent is extended or adjusted under 35 U.S.C. 154(b) by 663 days.

(21) Appl. No.: 16/946,462

(22) Filed: Jun. 23, 2020

Related U.S. Application Data (60) Provisional application No. 62/866,191, filed on Jun. 25, 2019.

(51) Int. Cl.
 *A61N 1/05* (2006.01)
 *A61K 47/02* (2006.01)
 *A61K 31/573* (2006.01)
 *A61N 1/36* (2006.01)

(52) U.S. Cl.
 CPC .......... *A61N 1/0556* (2013.01); *A61K 31/573* (2013.01); *A61K 47/02* (2013.01); *A61N 1/3605* (2013.01)

(58) Field of Classification Search
 CPC ............................ A61N 1/0556; A61N 1/0568
 See application file for complete search history.

(56) References Cited

U.S. PATENT DOCUMENTS

| 5,487,756 A | 1/1996 | Kallesoe et al. |
| 5,824,027 A | 10/1998 | Hoffer et al. |
| 7,596,414 B2 | 9/2009 | Whitehurst et al. |
| 8,423,157 B2 | 4/2013 | Moffitt et al. |
| 9,055,875 B2 | 6/2015 | Triantis et al. |
| 9,700,716 B2 | 7/2017 | Faltys et al. |
| 9,713,708 B2 | 7/2017 | Durand et al. |
| 2007/0198063 A1* | 8/2007 | Hunter ............... A61N 1/37512 607/3 |
| 2008/0172116 A1* | 7/2008 | Mrva .................. A61N 1/0526 607/115 |
| 2010/0241207 A1 | 9/2010 | Bluger |
| 2015/0196515 A1* | 7/2015 | Aliyar ..................... A61P 31/10 156/60 |
| 2015/0202433 A1 | 7/2015 | Franke et al. |

(Continued)

OTHER PUBLICATIONS

Herrlich et al., Drug Release Mechanisms of Steroid Eluting Rings in Cardiac Pacemaker Lead Electrodes, 34th Annual International Conference of the Institute of Electrical and Electronics Engineers Engineering in Medicine and Biology Society, 2012, pp. 681-684.

*Primary Examiner* — Catherine M Voorhees
*Assistant Examiner* — Elizabeth K So
(74) *Attorney, Agent, or Firm* — Kilpatrick Townsend & Stockton LLP (57) ABSTRACT

A implantable neural electrode assembly is described. The implantable neural electrode assembly includes a plurality of open-ended rings alternatingly connected to a spine. An inner layer of the open-ended rings is formed from a drug-loaded material (e.g., silicone that has been loaded with a steroid) and an outer layer is formed from a drug-free material. One or more electrode assemblies are connected to the inner layer and oriented towards a center of a cylinder defined by the plurality of open-ended rings.

17 Claims, 6 Drawing Sheets

(56) References Cited

U.S. PATENT DOCUMENTS

2017/0266436 A1    9/2017  Suwito et al.
2018/0117313 A1*   5/2018  Schmidt ............... A61N 1/3752
2020/0230421 A1*   7/2020  Zaidi ..................... A61N 1/372

* cited by examiner

FIG. 7

BI-LAYERED NEURAL INTERFACE WITH NERVE-FACING DRUG ELUTING STRUCTURE

CROSS-REFERENCE TO RELATED APPLICATIONS

This application claims priority to U.S. Provisional Patent Application No. 62/866,191, filed on Jun. 25, 2019, the entire contents of which are hereby incorporated by reference in their entirety.

BACKGROUND

Fibrosis is the formation of excess fibrous connective tissue. A certain type of fibrosis is reactive to injury to the tissue and is typically referred to as scarring. When a medical implant is placed in a human's body, tissue surrounding the implant location is injured, which causes a fibrotic response. This response may cause additional scarring at the implant location during the lifetime of the implant. Steroids and other drugs may be used to slow down and/or eliminate the fibrotic response at the implant location.

BRIEF SUMMARY

Various examples are described relating to implantable neural electrode assemblies, systems including implantable neural electrode assemblies, and methods for forming and using implantable neural electrode assemblies.

One general aspect includes an electrode assembly, including a spine to support a lead conductor and a first open-ended ring connected to the spine. The first open-ended ring includes a first layer defining an interior surface of the first open-ended ring, the first layer formed from a drug-loaded silicone, and the interior surface oriented toward a center of the first open-ended ring. The first open-ended ring also includes a first electrode fixedly supported by the first layer and disposed at the interior surface, the first electrode configured to electrically connect to the lead conductor. The electrode assembly also includes a second layer defining an exterior surface of the first open-ended ring, the second layer formed from a drug-free silicone, the exterior surface oriented away from the center of the first open-ended ring.

Another general aspect includes a method, including forming a first concentric layer of an open-ended ring neural cuff using a drug-loaded silicone, the first concentric layer including a first side facing a center of the open-ended ring neural cuff, and a second side oriented opposite the first side. The method also includes connecting an electrode to the first concentric layer such that an electrode surface of the electrode is oriented toward the center. The method also includes electrically connecting the electrode to a lead conductor. The method also includes forming a second concentric layer of the open-ended ring neural cuff, the second concentric layer including a third side that coats at least the second side of the first concentric layer.

Another general aspect includes a method, including providing an open-ended ring neural cuff that includes a spine, a plurality of open-ended rings that are axially aligned with each other, with respective ends alternatingly connected to the spine, at least one open-ended ring of the plurality of open-ended rings including a drug-loaded inner layer, an electrode supported by the drug-loaded inner layer, and a drug-free outer layer. The method also includes implanting the open-ended ring neural cuff within a subject. The method also includes positioning the open-ended ring neural cuff axially around a portion of a nerve structure of the subject.

Another general aspect includes a system, including an neural cuff assembly that includes a spine, one or more open-ended ring structures connected to the spine, at least one open-ended ring structure of the one or more open-ended ring structure including an inner layer formed from a drug-loaded material and an outer layer formed from a drug-free material. Neural cuff assembly also includes an electrode supported by the inner layer of the at least one open-ended ring structure. The system also includes a lead conductor electrically connected to the electrode. The system also includes a plug disposed at a distal end of the lead conductor, the plug electrically connected to the lead conductor.

Another general aspect includes a system, including means for outputting one or more electrical signals. The system also includes supporting means for supporting the means for outputting. The supporting means formed from a drug-loaded silicone and a drug-free silicone. The means for outputting one or more electrical signals connected to the supporting means. The system also includes signal generating means for generating the one or more electrical signals. The system also includes connecting means for electrically connecting the signal generating means and the means for outputting one or more electrical signals.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

DETAILED DESCRIPTION

Examples are described herein in the context of electrode assemblies and, in particular, electrode assemblies that are implantable within a person's body for peripheral nerve stimulation. Those of ordinary skill in the art will realize that the following description is illustrative only and is not intended to be in any way limiting. For example, the features described with respect to the implantable electrode assemblies for peripheral nerve stimulation are applicable to any other electrode that is implanted into a person's body at locations other than peripheral nerves. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In a conventional neuromodulation system, an electrode (e.g., included in a neural interface) that is electrically connected to a pulse generator device may be implanted in the body at or around a nerve at an implant location. Generally, to stimulate the nerve, electrical signals are generated by the pulse generator device and delivered to the nerve via the electrode. Because of the body's fibrotic response to the presence of the electrode (e.g., a type of injury), scar tissue may begin to form at the implant location. In some cases, the scar tissue may continue to grow over time. This scar tissue may provide the benefit of retaining the electrode at the implant location. Undesirably, however, the presence of scar tissue between the nerve and the electrode may impact the ability of the electrode to deliver appropriate electrical signals to the nerve. For example, electrode-tissue impedance increases with the amount of fibrotic (e.g., scar) tissue formed between the electrode and the target nerve or neurovascular bundle of interest. To account for this increase in impedance and still deliver electrical signals within some predefined voltage range, the pulse generator device outputs electrical signals at a higher current. This may be undesirable and/or impossible because (i) the pulse generator device may be unable to output a suitably high current, (ii) outputting the required current may result in undesirable power consumption at the pulse generator device, given the voltage constraints—the pulse generator device may be unable to deliver enough current for effective therapies, and/or (iii) outputting the required current may exceed a material constraint on the system and thereby damage some part of the system (e.g., corresponding high voltage may damage parts of the electrode).

In an illustrative example, an implantable neural electrode assembly has the form factor of a cuff including multiple open-ended ring structures that are individually openable to wrap around a nerve during implantation. The open-ended ring structures are formed from two layers of material, a drug-loaded inner layer (e.g., a silicone layer including a steroid drug) that supports electrodes and a drug-free outer layer (e.g., a silicone layer that excludes the steroid drug) that surrounds the drug-loaded inner layer. When implanted, the drug-loaded inner layer of the open-ended ring structures is nearest to and faces the nerve. This allows for targeted delivery of the drug to tissue located between the electrodes and the nerve. For example, the drug in the drug-loaded inner layer may be distributed over time via elution to this tissue. This distribution of the drug slows down and/or eliminates the body's fibrotic response in this tissue, which results in little or no formation of scar tissue in this tissue. At the same time, the drug-free outer layer of the open-ended ring structures, which is furthest from the nerve, is surrounded by other tissue. Because the drug-free outer layer does not include a steroid drug, this arrangement does not impede the body's natural fibrotic response in the other tissue surrounding the drug-free outer layer. This arrangement effectively results in targeted growth of scar tissue in the volume of tissue that surrounds the drug-free outer layer. This scar tissue may help to retain the implantable neural electrode assembly in place while, at the same time, not impacting the performance of the implantable neural electrode assembly.

This illustrative example is given to introduce the reader to the general subject matter discussed herein and the disclosure is not limited to this example. The following sections describe various additional non-limiting examples of implantable neural electrode assemblies.

Figure 1:
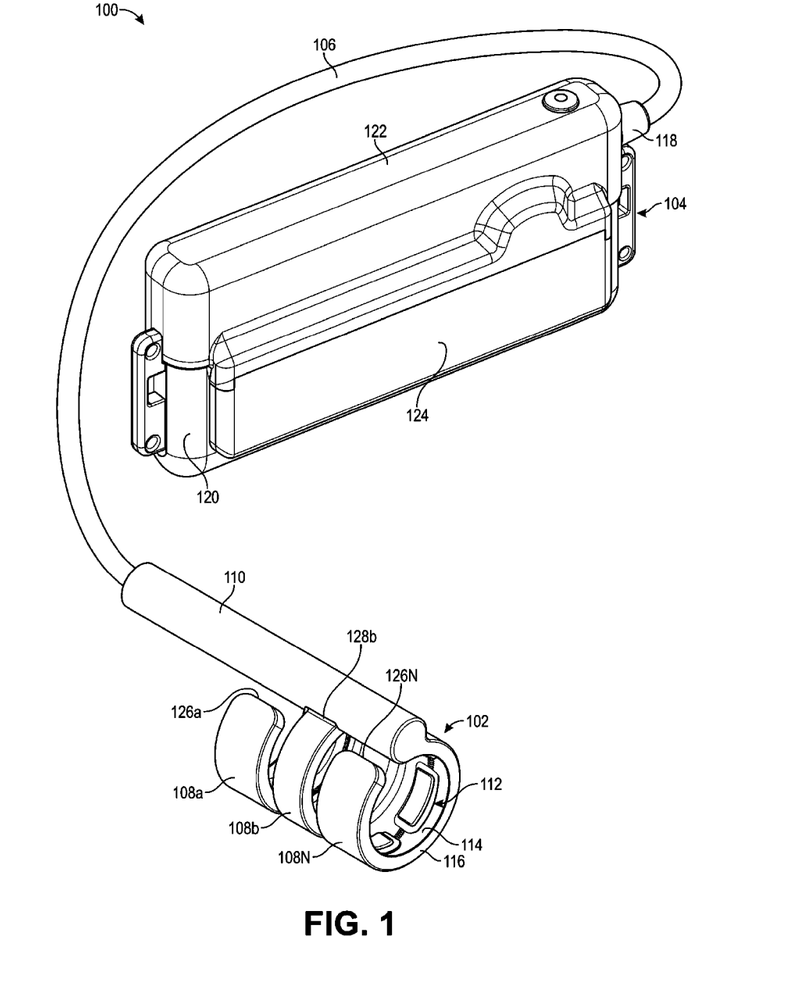
FIG. 1 illustrates a perspective view of a system including an implantable neural electrode assembly, according to at least one example.

Referring now to the figures, FIG. 1 illustrates a perspective view of a neuromodulation system 100 including an implantable neural electrode assembly 102, according to at least one example. The neuromodulation system 100 also includes a pulse generator device 104 electrically connected to the implantable neural electrode assembly 102 (e.g., a neural interface) via a lead conductor 106. The neuromodulation system 100 may be implantable in a human subject's tissue to perform one or more neuromodulation therapies. For example, the implantable neural electrode assembly 102 may be placed at a target location within the subject's body and, depending on the target location, the pulse generator device 104 may be placed adjacent to the implantable neural electrode assembly 102 or may be spaced apart from the implantable neural electrode assembly 102 at some distance. The pulse generator device 104 then delivers electrical signals to the target location using the implantable neural electrode assembly 102 and records responses collected by the implantable neural electrode assembly 102.

The neuromodulation system 100 is configured to perform neuromodulation therapies at nerves that are part of the peripheral nervous system (e.g., nerves that are located beyond the brain or spinal cord). This may enable targeted therapies to treat pain and affect functions of other body systems such as treat overactive bladder disorder and autoimmune disorders. In some examples, the neuromodulation system 100 may be configured to perform neuromodulation therapies at locations other than the peripheral nervous system. For example, the neuromodulation system 100 may be used for neuromodulation of the Vagus nerve.

Turning now to the implantable neural electrode assembly 102, the implantable neural electrode assembly 102 includes one or more open-ended rings 108a-108N each connected to a spine 110. The open-ended ring 108N may be connected to the spine 110 at a distal end of the implantable neural electrode assembly 102. The open-ended rings 108 are alternatingly connected to the spine 110. For example, open ends 126a and 126N of the open-ended rings 108a and 108N curve towards, but do not connect with, the spine 110. Opposite connected or closed ends of the open-ended rings 108a and 108N are connected to the spine 110 at an opposite side of the spine 110. Similarly, a connected end 128b of the open-ended ring 108b is connected to the spine 110, while an opposite open end of the open-ended ring 108b curves towards, but does not connect with, the spine 110 at an opposite side of the implantable neural electrode assembly 102. This arrangement may be suitable for placing the implantable neural electrode assembly 102 axially around a nerve. In some examples, all of the open-ended rings 108 may have open ends 126 connected on the same side of the spine 110, i.e., may not be alternatingly connected to the spine 110.

At least one of the open-ended rings 108 includes and structurally supports an electrode assembly 112, e.g., the open-ended rings 108a and 108N include electrode assemblies 112 in the implantable neural electrode assembly 102 illustrated in FIG. 1. The electrode assemblies 112 are used to deliver electrical signals received from the pulse generator device 104 to a target location in the subject's body. In the illustrated example, the open-ended rings 108a and 108N each include an electrode assembly 112 including more than one electrode and the open-ended ring 108b includes no electrode assembly 112. In some examples, the implantable neural electrode assembly 102 includes a single open-ended ring 108 including an electrode assembly 112 including one or more electrodes or multiple open-ended rings 108 each including an electrode assembly 112 including one or more electrodes. The number of open-ended rings 108 and the number of electrode assemblies 112 (and electrodes of the electrode assemblies 112) may depend on the target location, the desired neuromodulation therapy, and certain design considerations such as size, bulk, etc. In some examples, instead of the open-ended rings 108 being formed into a cuff, the electrode assemblies 112 may be supported by other suitable structures such as flat electrode paddles. In some examples, the electrodes paddles may be arranged along an open-ended ring formed from a piece of rigid material.

The implantable neural electrode assembly 102 is formed from at least two material layers, an inner layer 114 and an outer layer 116. The inner layer 114 provides structural support for the electrode assemblies 112. The inner layer 114 is formed from a drug-loaded material such as a silicone that has been loaded with a steroid drug (e.g., the drug-loaded inner layer 114). The outer layer 116 is formed from a drug-free material such as a silicone that has not been loaded with a steroid drug (e.g., the drug-free outer layer 116). The structure and function of the open-ended rings 108, including the electrode assemblies 112 and the layers 114 and 116, will be discussed in detail with respect to other figures.

In practice, the implantable neural electrode assembly 102 is implanted at a target location within tissue of a human body (e.g., a location where neuromodulation is to occur) and the implantable neural electrode assembly 102 is connected to a nerve at the target location. To connect the implantable neural electrode assembly 102 with the nerve, ends of the open-ended rings 108 are deflected away from the spine 110 to "open" the cuff. This enables the implantable neural electrode assembly 102 to be placed around the nerve such that the nerve extends axially within a cylindrical volume defined by the open-ended rings 108.

Generally, the spine 110 provides structural support for the open-ended rings 108 and extends around a portion of the lead conductor 106. The lead conductor 106 includes one or more electrical wires encased in a pliable material such as silicone. Electrical signals are transported by the electrical wires between the implantable neural electrode assembly 102 and the pulse generator device 104. The lead conductor 106 includes a plug 118 configured for installation into a port of the pulse generator device 104. The implantable neural electrode assembly 102 and the lead conductor 106 are electrically and mechanically coupled to form a single apparatus that may be removably coupled to the pulse generator device 104 using the plug 118 and the port. In some examples, the lead conductor 106 may be its own separate part that is electrically and mechanically coupled to the implantable neural electrode assembly 102 at a first end and electrically and mechanically coupled to the pulse generator device 104 at a second end as part of implanting the neuromodulation system 100. In some examples, the implantable neural electrode assembly 102, the lead conductor 106, and the pulse generator device 104 (e.g., the entirety of the neuromodulation system 100) may be electrically and mechanically coupled to form a single apparatus prior to implantation.

Turning now to the pulse generator device 104, because the pulse generator device 104 will be inserted or otherwise implanted in the subject's skin, the pulse generator device 104 has a small form factor (e.g., about 40 mm long, about 20 mm tall, and about 7 mm wide in this example) and smooth edges to reduce the potential for subject irritation or injury during and after insertion. In some examples, the dimension of the pulse generator device 104 may be greater than those listed or smaller than those listed.

As illustrated in FIG. 1, generally, the pulse generator device 104 includes an enclosure 120 sometimes referred to as a canister, a header 122, and a communications antenna 124. The enclosure 120 is configured to house active components of the pulse generator device 104 such as one or more batteries and an electronics assembly. The enclosure 120 is hermetically sealed thereby keeping the active components free from moisture exposure. The enclosure 120 is formed from a metallic material such as Titanium or other biocompatible metallic material. In some examples, some or a portion of the enclosure 120 is formed from a different rigid material which may or may not be metallic such as a biocompatible epoxy.

The electronics assembly, which may be housed in the enclosure 120, includes one or more electronic components to perform signal processing, such as filtering, digitizing, performing fast Fourier transforms, etc. For example, the electronics assembly may include a system on chip ("SOC") or system in package ("SIP") that includes any suitable combination components for digital signal processing, analog signal processing, mixed-signal processing, and/or the like that may be present on the surface of a PCB assembly or embedded. Such components may include, for example, a microcontroller, a memory, a timing source, one or more digital interfaces, one or more analog interfaces, voltage regulators, and/or any other suitable component. The electronics assembly may be configured to receive electrical signals from the implantable neural electrode assembly 102, process such signals, and provide signals to the implantable neural electrode assembly 102.

In some examples, the electronics assembly includes a processing device and a computer-readable medium, such as a random access memory ("RAM") coupled to the processing device. The processing device may execute computer-executable program instructions stored in memory, such as executing one or more computer programs. Such processing devices may comprise a microprocessor, a digital signal processor ("DSP"), an application-specific integrated circuit ("ASIC"), field programmable gate arrays ("FPGAs"), state machines, or other processing means for processing electrical signals received from neural interface. Such processing means may further include programmable electronic devices such as PLCs, programmable interrupt controllers ("PICs"), programmable logic devices ("PLDs"), programmable read-only memories ("PROMs"), electronically programmable read-only memories ("EPROMs" or "EEPROMs"), or other similar devices.

The processing device may include, or may be in communication with, media, for example computer-readable storage media, that may store instructions that, when executed by the processing device, cause the processing device to perform steps as carried out, or assisted, by a processing device. Examples of computer-readable media may include, but are not limited to a memory chip, ROM, RAM, ASIC, or any other storage means from which a processing device can read or write information.

The header 122 is configured to encase other active and/or passive components such as a charging antenna and a connector stack for connecting to the plug 118 that are mounted to the enclosure 120. The header 122 is formed from a biocompatible material such as an epoxy. The header 122 is either formed in place or pre-formed and mounted to a lid of the enclosure 120. The header 122 is configured to encapsulate the connector stack and the charging antenna.

The communications antenna 124 is mounted to an exterior surface of the enclosure 120. The communications antenna 124 may be any suitable device for receiving and/or sending electrical signals operating according to the Bluetooth® standard. In some examples, the communications antenna 124 operates according to different standards or is configured differently. The communications antenna 124 functions to send and receive information relating to operation of the pulse generator device 104, e.g., parameters measured by the implantable neural electrode assembly 102, configuration data, state data, control signals, any other information relating to the neuromodulation system 100. The communications antenna 124 may enable pairing/communicating with a second device such as a programming unit, a charger, a mobile phone, or other device located outside the body. In some examples, the communications antenna 124 enables pairing/communicating with other devices located within the body.

Figure 2:
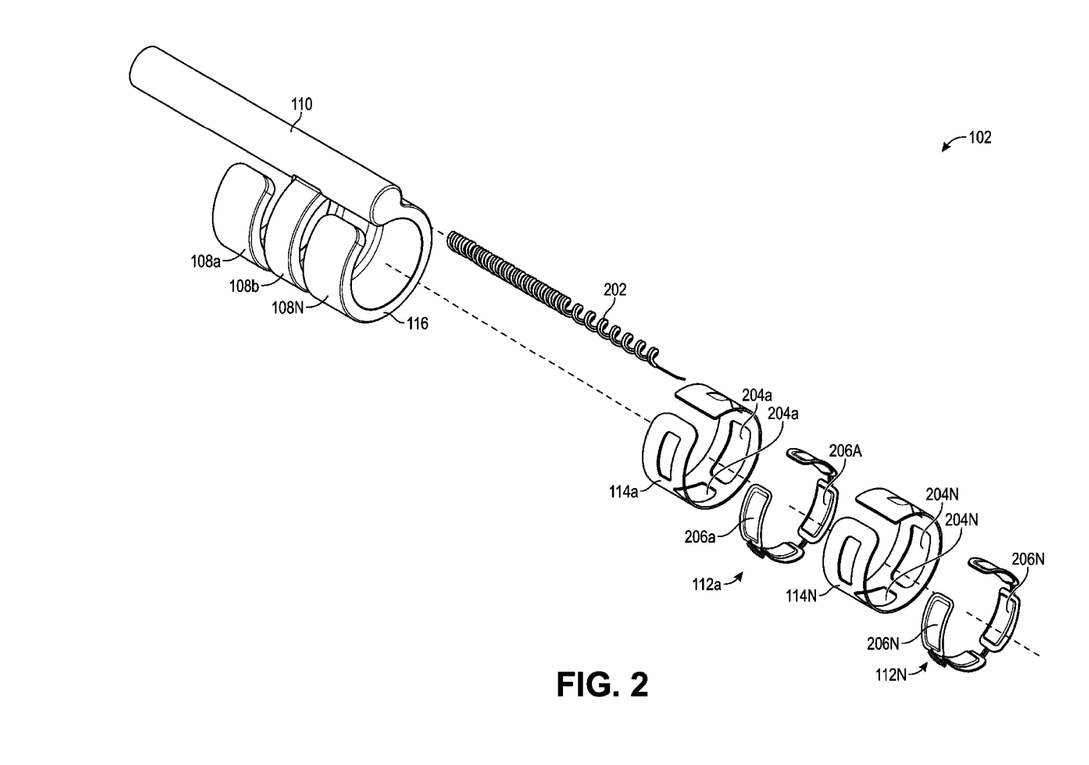
FIG. 2 illustrates an exploded view of the implantable neural electrode assembly of FIG. 1, according to at least one example.

Turning now to details of the implantable neural electrode assembly 102, FIG. 2. illustrates an exploded view of the implantable neural electrode assembly 102, according to at least one example. As illustrated, the implantable neural electrode assembly 102 includes a pair of drug-loaded inner layers 114a and 114N, a pair of corresponding electrode assemblies 112a and 112N, a wire assembly 202, and the drug-free outer layer 116 which forms the spine 110 and the open-ended rings 108. Because the implantable neural electrode assembly 102 will be inserted or otherwise implanted in the subject's skin, the implantable neural electrode assembly 102 has a small form factor (e.g., a length of about 10-11 mm, with each open-ended ring having a diameter of about 6-9 mm in this example) and smooth edges to reduce the potential for subject irritation or injury during and after insertion. In some examples, the dimension of the implantable neural electrode assembly 102 may be greater than those listed or smaller than those listed.

Figure 3A:
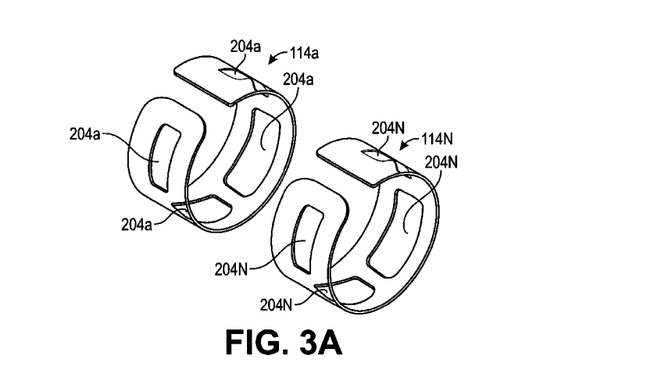
FIG. 3A illustrates a perspective view of a first state of formation of an implantable neural electrode assembly, according to at least one example.

The pair of drug-loaded inner layers 114a and 114N are illustrated in greater detail in FIG. 3A. In particular, FIG. 3A illustrates a perspective view of a first state of formation of the implantable neural electrode assembly 102, according to at least one example. At this first state, the pair of drug-loaded inner layers 114a and 114N are formed. The drug-loaded inner layers 114a-114N are numbered such to indicate that the implantable neural electrode assembly 102 may include any suitable number of drug-loaded inner layers 114 corresponding to the open-ended rings 108. For example, the implantable neural electrode assembly 102 may include one drug-loaded inner layer 114 and one open-ended ring 108, two drug-loaded inner layers 114 and two open-ended rings 108, or more than two drug-loaded inner layers 114 and more than two open-ended rings 108. Similar notation (e.g., "a-N") is used throughout this specification to illustrate when any suitable number of elements may be included.

The drug-loaded inner layers 114 are formed from a biocompatible silicone that is loaded with an anti-inflammatory steroid that reduces formation of scar tissue. In some examples, the steroid may be Dexamethasone Acetate (DXA) or other drug having anti-inflammatory properties.

The biocompatible silicone used to form the drug-loaded inner layers 114 may include MED-4870 manufactured by Nusil™, Bluestar LSR D125M manufactured by Elkem® Silicones, or any other long-term implantable silicones having similar properties. The silicone may be loaded with the drug using any suitable technique. For example, the drug may be mixed into a liquid form of the silicone to create a homogenous mix. The concentration of the steroid may be varied depending on the implementation. For example, the concentration of the steroid may be within a range of 1%-20%.

In some examples, the drug may be formed into small beads (e.g., around 1.0 mm in diameter) and placed into holes present on the surface of the silicone that faces the nerve. The holes may be formed as part of a post-processing step after the silicone has been formed into the shape which will result in the drug-loaded inner layers 114 or during the injection molding.

The drug-loaded inner layers 114 may be capable of eluting their drugs at least because the drugs are released from the drug-loaded inner layers 114 using the process of elution (e.g., the process of extracting one material from another by washing with a solvent). In this example, when the implantable neural electrode assembly 102 is implanted in the body, interstitial fluid (e.g., a solvent) in the body will wash over drug-loaded inner layers 114 and extract the drug from the drug-loaded inner layers 114 over time. Because the drug-free outer layers 116 surround the drug-loaded inner layers 114, the drug that is washed from the drug-loaded inner layers 114 interacts with the tissue that is nearest the drug-loaded inner layers 114 (e.g., within a cylindrical volume defined by drug-loaded inner layers 114 of the open-ended rings 108). Typically, during implantation, the ends of the open-ended rings 108 are deflected away from the spine 110 to place the nerve axially within the cylindrical volume.

The drug-loaded inner layers 114 are formed using injection molding; although, other suitable formation techniques may also be used, in some examples. For example, the drug-loaded inner layers 114 may be molded around a core pin that goes between two halves of a mold. As illustrated in FIG. 3A, the drug-loaded inner layers 114 are generally ring shaped with open ends. The form of the drug-loaded inner layers 114 correspond to the form of the open-ended rings 108 formed from the drug-free outer layer 116. The mold halves may include ring-shaped interior surfaces to form the drug-loaded inner layers 114 into the generally ring shape. The mold halves may also include structures to form windows 204 in the drug-loaded inner layers 114.

Figure 3B:
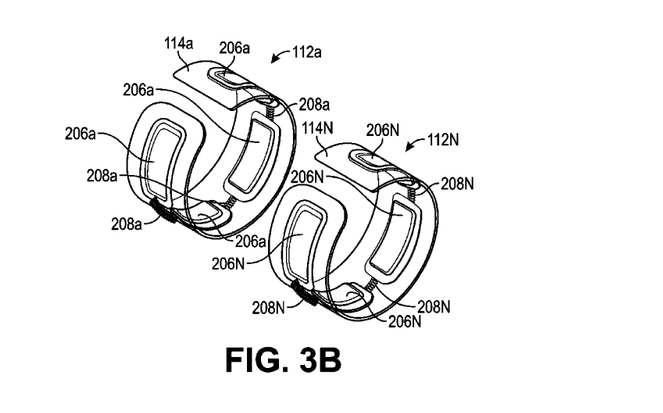
FIG. 3B illustrates a perspective view of a second state of formation of an implantable neural electrode assembly, according to at least one example.

As illustrated in FIG. 3A, the windows 204 extend completely through the drug-loaded inner layers 114. As illustrated in FIG. 3B, the windows 204 are sized and configured to receive electrodes 206 of the electrode assemblies 112. In particular, FIG. 3B illustrates a perspective view of a second state of formation of the implantable neural electrode assembly 102, according to at least one example. At this second state, the electrode assemblies 112 are connected to the drug-loaded inner layer 114. To form this connection, each electrode 206 may be inserted through a corresponding window 204 and glued to the drug-loaded inner layer 114. Each electrode 206 includes a flange that extends around a perimeter of the electrode 206. When an electrode 206 is installed in a window 204, a surface of the flange will contact the drug-loaded inner layer 114. Glue may be applied to this surface or the portion of the drug-loaded inner layer 114.

In some examples, each electrode 206 includes a pair of parallel flanges that extend around a perimeter of the electrode 206. When an electrode 206 is installed in a window 204, a portion of the drug-loaded inner layer 114 surrounding the window 204 may index into a space between the pair of parallel flanges. Glue may be applied to one or both sides of the drug-loaded inner layer 114 surrounding the window 204 and/or within the space between the pair of parallel flanges.

The electrodes 206 are any suitable electrode capable of delivering electrical signals to a human nervous system and/or registering electrical signals. In some examples, the electrodes 206 may be used for electrophysiological monitoring and/or for detecting and/or measuring substances in the human body (e.g., a glucose biosensor). Recording surfaces (e.g., inner surfaces) of the electrodes 206 are oriented inwardly and generally have a concave shape. These recording surfaces will face a nerve when the implantable neural electrode assembly 102 is implanted in the human subject. The outer surfaces (e.g., at an opposite side of the electrode 206) generally have a convex shape and covered by the drug-free outer layer 116.

In some examples, the electrodes 206 may have a different form factor than those illustrated. For example, the electrodes 206 may take the form of thin foil that wraps through the windows. The electrodes 206 may also take the form of spiral wire that extends through the open-ended rings 108.

In some examples, instead of the windows 204, the electrodes 206 may be glued directly to inner surfaces of the drug-loaded inner layer 114. In this example, small holes may be formed through the drug-loaded inner layer 114 through which wiring from the electrodes 206 may pass. This wiring may run along outer surfaces of the drug-loaded inner layer. The small holes may then be potted with silicone or other biocompatible material.

Individual electrodes 206 of the respective electrode assemblies 112 may be electrically connected using one or more connectors 208. For example, the connectors 208, which may include one or more electrical contacts, may be connected to one or more electrodes 206 using any suitable method for forming electrical connections. For example, the electrical connections may be formed using laser welding, crimping, soldering, or any other suitable mechanical and/or energetic method for forming electrical connections.

Figure 3C:
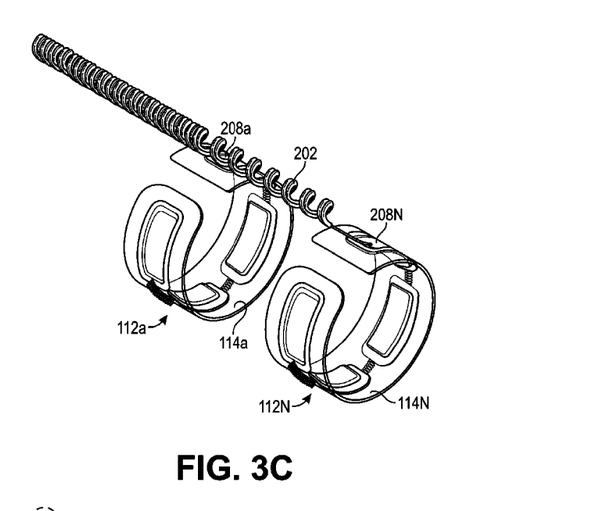
FIG. 3C illustrates a perspective view of a third state of formation of an implantable neural electrode assembly, according to at least one example.

As illustrated in FIG. 3B, the four electrodes 206a are electrically connected at three connection points using three connectors 208a. In some examples, fewer or more connectors 208 may be used. As illustrated in FIG. 3C, the use of the connectors 208 may enable a single connection between the wire assembly 202 and each of the electrode assemblies 112. In particular, FIG. 3C illustrates a perspective view of a third state of formation of the implantable neural electrode assembly 102, according to at least one example. At this third state, the electrode assemblies 112 are electrically connected to the wire assembly 202 at connection points formed by the connectors 208a and 208N. These connections may be achieved using any suitable method for forming electrical connections. For example, the connections may be formed using laser welding, crimping, soldering, or any other suitable mechanical and/or energetic method for forming electrical connections.

The wire assembly 202 is illustrated as being coiled and including four total wires, two for each of the electrode assemblies 112a and 112N. In some examples, the wire assembly 202 is stranded or takes some other form (e.g., wires within a lumen). The number of wires in the wire assembly 202 and the number of electrodes 206 may depend on the number of channels needed for a particular neuromodulation therapy. In some examples, each wire of the wire assembly 202 and one or more electrodes 206 may be devoted to a single channel. In some examples, each wire of the wire assembly 202 may be devoted to more than one channel. Techniques for transmitting electrical signals over multiple channels are well known.

Figure 3D:
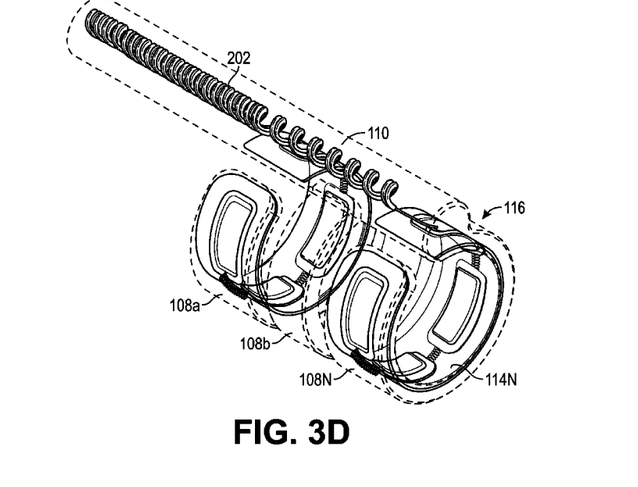
FIG. 3D illustrates a perspective view of a fourth state of formation of an implantable neural electrode assembly, according to at least one example.

Turning now to FIG. 3D, FIG. 3D illustrates a perspective view of a fourth state of formation of the implantable neural electrode assembly 102, according to at least one example. At this fourth state, the drug-free outer layer 116, which forms the spine 110 and outer portions of the open-ended rings 108, has been formed. The drug-free outer layer 116 is formed from biocompatible silicone such as MED-4870 manufactured by Nusil™, Bluestar LSR D125M manufactured by Elkem® Silicones, or any other suitable biocompatible silicone having similar properties.

The drug-free outer layer 116 is formed using injection molding; although, other suitable formation techniques may also be used, in some examples. For example, the drug-free outer layer 116 may be molded using the same core pin used to mold the drug-loaded inner layers 114, but a different mold set. The mold set may allow for over molding of the drug-free outer layer 116. Over molding of the wire assembly 202 forms the spine 110 and over molding outer surfaces of the drug-loaded inner layers 114 (e.g., an outer surface of the drug-loaded inner layers 114 and cylindrical top and bottom edges of the drug-loaded inner layers 114) forms the open-ended rings 108.

As illustrated in FIG. 3D, the drug-loaded inner layer 114 is concentric with the portion of the drug-free outer layer 116 that forms the open-ended rings 108, with the drug-loaded inner layer 114 being nearer the center than the drug-free outer layer 116. In some examples, the drug-free outer layer 116 is thicker than the drug-loaded inner layer 114. Encapsulation of the cylindrical top and bottom edges of the drug-loaded inner layers 114 with the drug-free outer layer 116 improves the accuracy with which the drug may be delivered to a nerve located within the open-ended rings 108. In particular, because the cylindrical edges are covered by the drug-free outer layer 116, the drug is unable to elute via the cylindrical edges but instead must be directed through the inner surfaces of the drug-loaded inner layer 114. In some examples, because the drug-free outer layer 116 does not have drugs, a fibrotic response will naturally occur in the volume of tissue surrounding the drug-free outer layer 116. Scar tissue formed by the fibrotic response may function to retain the implantable neural electrode assembly 102.

In some examples, the drug-free outer layer 116 and the drug-loaded inner layers 114 may be formed as part of a flat sheet, with the drug-free outer layer 116 being pre-tensioned to cause the open-ended ring shape. For example, the drug-loaded inner layers 114 may be formed as a flat sheet and the electrodes 206 may be connected to the flat sheet as described herein. Afterwards, the drug-free outer layer 116 may pre-tensioned and connected (e.g., glued or otherwise adhered) to the drug-loaded inner layer 114. Because the drug-free outer layer 116 is pre-tensioned, the drug-free outer layer 116 may cause the drug-loaded inner layer 114 and the drug-free outer layer 116 to curl inwards to form a shape similar to the open-ended rings 108.

Figure 4:
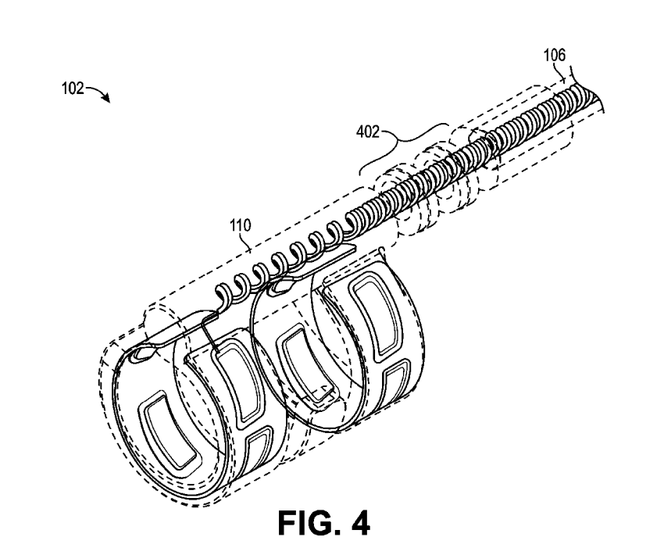
FIG. 4 illustrates a perspective view of an implantable neural electrode assembly including a compliant joint, according to at least one example.
Figure 5:
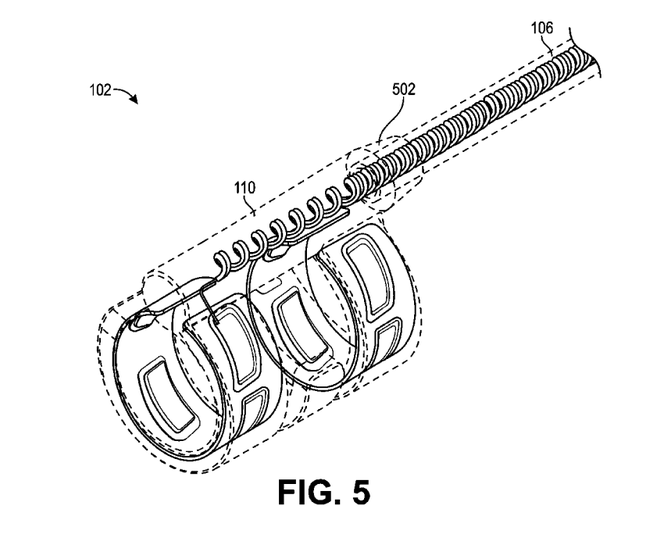
FIG. 5 illustrates a perspective view of an implantable neural electrode assembly including a compliant joint, according to at least one example.

FIGS. 4 and 5 illustrate perspective views of the implantable neural electrode assembly 102, respectively, including a compliant joint 402 and a compliant joint 504, according to various examples. In particular, in FIG. 4, the spine 110 includes the compliant joint 402. The compliant joint 402 takes the form of a plurality of concentric cylinders of varying sizes stacked end to end. The compliant joint 402 provides strain relief at a location where the spine 110 connects to the lead conductor 106. The compliant joint 502 has a conical shape, with a larger end nearer the open-ended rings 108. The compliant joint 502 provides strain relief at a location where the spine 110 connects to the lead conductor 106.

Figure 6:
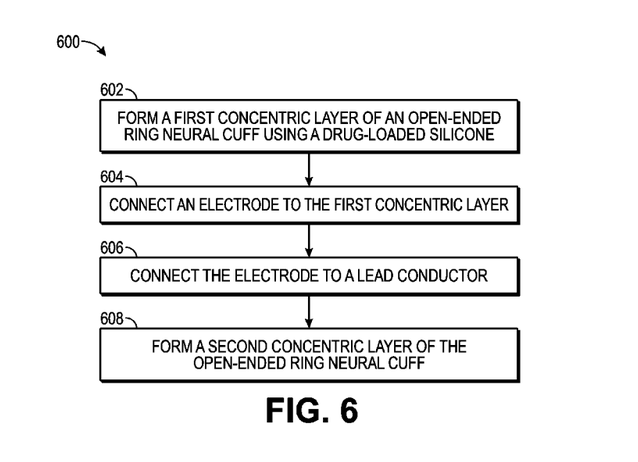
FIG. 6 illustrates a flow chart showing a process for forming an implantable neural electrode assembly, according to at least one example.

FIG. 6 illustrates a flow chart showing a process 600 for forming an implantable neural electrode assembly such as the implantable neural electrode assembly 102, according to at least one example. The process 600 begins at block 602 by forming a first concentric layer (e.g., the drug-loaded inner layer 114) of an open-ended ring neural cuff using a drug-loaded silicone. The first concentric layer may include a first side facing a center of the open-ended ring neural cuff and a second side oriented opposite the first side. The first concentric layer may formed using injection molding. The first concentric layer may include one or more windows. The windows may be formed with respect to the block 602 or as part of a post-processing technique (e.g., after the first concentric layer has been formed, the windows may be cut out using a punch and die, knife, or other suitable technique).

At block 604, the process 600 includes connecting an electrode to the first concentric layer. The electrode may be connected such that an electrode surface of the electrode is oriented toward the center of the open-ended ring neural cuff. In some examples, connecting the electrode to the first concentric layer may include gluing the electrode to the first concentric layer. In some examples, connecting the electrode includes installing the electrode within a window formed in the first concentric layer.

At block 606, the process 600 includes connecting the electrode to a lead conductor. This may include electrically connecting the electrode to the lead conductor. This may include using at least one of crimping, soldering, or laser welding.

At block 608, the process 600 includes forming a second concentric layer of the open-ended ring neural cuff. The second concentric layer may include a third side that coats at least the second side of the first concentric layer. The second concentric layer may be formed using injection molding. In some examples, the second concentric layer is formed from a second a drug-free silicone that is of the same type of silicone as the drug-loaded silicone used to form the first concentric layer. In some examples, forming the second concentric layer of the open-ended ring neural cuff may include forming an open-ended ring support structure (e.g., an open-ended ring 108). In this example, a first side of the open-ended ring support structure may face a center of the open-ended ring support structure and a second side may be oriented opposite the first side.

Figure 7:
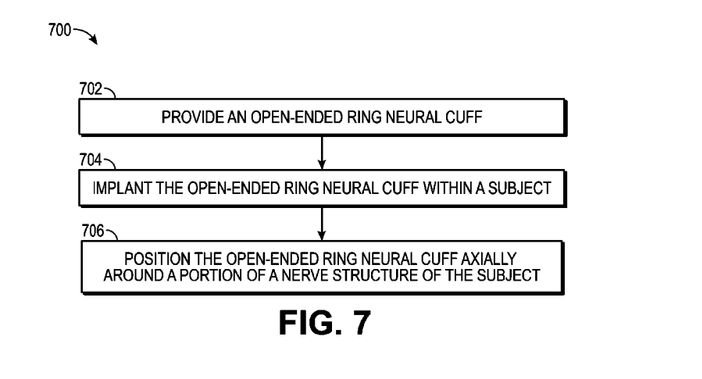
FIG. 7 illustrates a flow chart showing a process for implanting an implantable neural electrode assembly, according to at least one example.

FIG. 7 illustrates a flow chart showing a process 700 for implanting an implantable neural electrode assembly such as the implantable neural electrode assembly 102, according to at least one example. The process 700 may be performed by a medical professional. The process 700 begins at block 702 by providing an open-ended ring neural cuff (e.g., the implantable neural electrode assembly 102). The open-ended ring neural cuff may include a spine (e.g., the spine 110) and a plurality of open-ended rings (e.g., the open-ended rings 108) that are axially aligned with each other. As illustrated in FIG. 1, respective ends of the plurality of open-ended rings may be alternatingly connected to the spine. At least one open-ended ring of the plurality of open-ended rings may include an drug-loaded inner layer, an electrode supported by the drug-loaded inner layer, and a drug-free outer layer. In some examples, the drug-free outer layer may be coupled to the drug-loaded inner layer.

At block 704, the process 700 includes implanting the open-ended ring neural cuff within a subject such as a human subject or other mammalian subject.

At block 706, the process 700 includes positioning the open-ended ring neural cuff axially around a portion of a nerve structure of the subject. In some examples, this positioning may place the nerve structure axially within the open-ended ring neural cuff. In some examples, the nerve structure may be a nerve of a peripheral nervous system of the subject. In some examples, positioning the open-ended neural cuff may include deflecting the opposite ends to place the nerve structure within the plurality of open-ended rings.

In some examples, the process 700 may further include providing a pulse generator device (e.g., the pulse generator device 104), implanting the pulse generator device within the subject, and electrically connecting the open-ended ring neural cuff and the pulse generator device. In some examples, the open-ended ring neural cuff may additionally include a lead body connected to the spine. In this example, electrically connecting the open-ended ring neural cuff and the pulse generator device may include electrically connecting the lead body to the pulse generator device.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated examples thereof are shown in the drawings and have been described above in detail. It should be understood, however, that there is no intention to limit the disclosure to the specific form or forms disclosed, but on the contrary, the intention is to cover all modifications, alternative constructions and equivalents falling within the spirit and scope of the disclosure, as defined in the appended claims.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (e.g., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is otherwise understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

Preferred examples of this disclosure are described herein, including the best mode known to the inventors for carrying out the disclosure. Variations of those preferred examples may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An electrode assembly, comprising:
    a spine to support a lead conductor; and
    a first open-ended ring comprising a first connected end connected to the spine and a first open end, the first open-ended ring comprising:
        a first layer defining an interior surface of the first open-ended ring, the first layer formed from a drug-loaded silicone, the interior surface oriented toward a center of the first open-ended ring;
        a first electrode fixedly supported by the first layer and disposed at the interior surface, the first electrode configured to electrically connect to the lead conductor; and
        a second layer defining an exterior surface of the first open-ended ring, the second layer formed from a drug-free silicone, the exterior surface oriented away from the center of the first open-ended ring.

2. The electrode assembly of claim 1, wherein the first layer is coupled to the second layer.

3. The electrode assembly of claim 1, wherein the drug-loaded silicone is loaded with an anti-inflammatory steroid.

4. The electrode assembly of claim 3, wherein the anti-inflammatory steroid is Dexamethasone Acetate (DXA).

5. The electrode assembly of claim 1, further comprising a second open-ended ring comprising a second connected end connected to the spine and a second open end, the second open-ended ring comprising:
    a third layer defining an interior surface of the second open-ended ring, the third layer formed from the drug-loaded silicone;
    a second electrode fixedly supported by the third layer and disposed at the interior surface of the second open-ended ring; and
    a fourth layer defining an exterior surface of the second open-ended ring, the fourth layer formed from the drug-free silicone.

6. The electrode assembly of claim 5, further comprising a third open-ended ring comprising a third connected end connected to the spine and a third open end, the third open-ended ring formed from the drug-free silicone.

7. The electrode assembly of claim 6, wherein the first open-ended ring is positioned distally relative to the second open-ended ring, and the third open-ended ring is positioned between the first open-ended ring and the second open-ended ring.

8. The electrode assembly of claim 1 further comprising the lead conductor.

9. The electrode assembly of claim 8, wherein the first open-ended ring further comprises a second electrode fixedly supported by the first layer and disposed at the interior surface, the second electrode electrically connected to the lead conductor.

10. The electrode assembly of claim 8, wherein the first electrode comprises an electrode surface defined at a first side and one or more electrode leads positioned on a second opposite side, and wherein the electrode surface is oriented toward a center of the first open-ended ring and the first electrode is electrically connected to the lead conductor via the one or more electrode leads.

11. The electrode assembly of claim 1, wherein the second layer comprises an overmold.

12. The electrode assembly of claim 11, wherein the overmold forms the spine and encases the lead conductor.

13. The electrode assembly of claim 1, wherein the first layer comprises a first side and a second side, the interior surface is defined at the first side of the first layer, and the second layer encases the second side of the first layer.

14. The electrode assembly of claim 1, wherein a window is formed in the first layer and the first electrode is fixedly supported within the window.

15. The electrode assembly of claim 1, wherein, when the electrode assembly is implanted in tissue of a subject, the drug-loaded silicone releases drugs through the interior surface without releasing the drugs through the exterior surface.

16. The electrode assembly of claim 15, wherein releasing the drugs through the interior surface prevents fibrosis in the tissue of the subject.

17. The electrode assembly of claim 1, wherein the spine and the first open-ended ring are sized and configured for implantation in tissue of a subject.

* * * * *